(12) United States Patent
Matousek et al.

(10) Patent No.: US 10,942,123 B2
(45) Date of Patent: Mar. 9, 2021

(54) DETECTION OF PH

(71) Applicant: UNITED KINGDOM RESEARCH AND INNOVATION, Swindon (GB)

(72) Inventors: Pavel Matousek, Cumnor (GB); Nicholas Stone, Exeter (GB); Benjamin Gardner, Exeter (GB)

(73) Assignee: UNITED KINGDOM RESEARCH AND INNOVATION, Swindon (GB)

( * ) Notice: Subject to any disclaimer, the term of this patent is extended or adjusted under 35 U.S.C. 154(b) by 0 days.

(21) Appl. No.: 16/345,061

(22) PCT Filed: Oct. 27, 2017

(86) PCT No.: PCT/GB2017/053241
§ 371 (c)(1),
(2) Date: Apr. 25, 2019

(87) PCT Pub. No.: WO2018/078381
PCT Pub. Date: May 3, 2018

(65) Prior Publication Data
US 2019/0277766 A1    Sep. 12, 2019

(30) Foreign Application Priority Data
Oct. 28, 2016  (GB) ...................... 1618260

(51) Int. Cl.
*G01J 3/44* (2006.01)
*G01N 21/65* (2006.01)
*G01N 33/483* (2006.01)

(52) U.S. Cl.
CPC ........... *G01N 21/658* (2013.01); *G01N 21/65* (2013.01); *G01N 33/4833* (2013.01); *G01N 2201/068* (2013.01); *G01N 2201/126* (2013.01)

(58) Field of Classification Search
CPC .. G01N 21/658; G01N 21/65; G01N 33/4833; G01N 2201/068; G01N 21/64; G01J 3/44
See application file for complete search history.

(56) References Cited

U.S. PATENT DOCUMENTS

| | | |
|---|---|---|
| 5,046,854 A | 9/1991 | Weller et al. |
| 5,272,334 A | 12/1993 | Sai |

(Continued)

FOREIGN PATENT DOCUMENTS

| | | |
|---|---|---|
| EP | 0300529 A1 | 1/1989 |
| WO | 94/25861 | 11/1994 |

(Continued)

OTHER PUBLICATIONS

Abu-Absi et al., "Real Time Monitoring of Multiple Parameters in Mammalian Cell Culture Bioreactors Using an In-Line Raman Spectroscopy Probe," Biotechnology and Bioengineering, pp. 1-7 (2010).

(Continued)

*Primary Examiner* — Abdullahi Nur
(74) *Attorney, Agent, or Firm* — Preti Flaherty Beliveau & Pachios LLP

(57) ABSTRACT

We disclose methods and apparatus for measuring pH in a sub-surface volume of a diffusely scattering sample. Probe light is directed to an entry region on the sample surface, and collected from a collection region on the sample surface following diffuse scattering within the sample. The collection region is spatially offset from the entry region, so that when one or more Raman spectral features are detected in the collected probe light, a pH of the sub-surface volume can be determined from the spectral features.

35 Claims, 10 Drawing Sheets

(56) References Cited

U.S. PATENT DOCUMENTS

| | | | |
|---|---|---|---|
| 5,553,616 | A | 9/1996 | Ham et al. |
| 6,070,093 | A | 5/2000 | Oosta et al. |
| 6,377,828 | B1 | 4/2002 | Chaiken et al. |
| 6,567,678 | B1 | 5/2003 | Oosta et al. |
| 6,868,285 | B2 | 3/2005 | Muller-Dethlefs |
| 6,992,759 | B2 | 1/2006 | Nakayama et al. |
| 7,413,341 | B1 | 8/2008 | Kachynski et al. |
| 7,475,724 | B2 | 1/2009 | Pribnow et al. |
| 8,243,269 | B2 | 8/2012 | Matousek et al. |
| 8,902,425 | B2 | 12/2014 | Babic |
| 9,778,172 | B2 | 10/2017 | Pelletier et al. |
| 2003/0174384 | A1 | 9/2003 | Halas et al. |
| 2005/0117150 | A1* | 6/2005 | Puppels ................. G01N 21/65 356/301 |
| 2007/0027373 | A1 | 2/2007 | Xie |
| 2007/0282182 | A1 | 12/2007 | Messerges et al. |
| 2008/0076985 | A1* | 3/2008 | Matousek ............ A61B 5/0059 600/310 |
| 2008/0204742 | A1 | 8/2008 | Halas et al. |
| 2008/0246947 | A1 | 10/2008 | Lees et al. |
| 2009/0022204 | A1 | 1/2009 | Kurth et al. |
| 2010/0011769 | A1 | 1/2010 | Gambacorta et al. |
| 2010/0049007 | A1 | 2/2010 | Sterling et al. |
| 2010/0145200 | A1 | 6/2010 | Mahadevan-Jansen et al. |
| 2011/0213216 | A1 | 9/2011 | McKenna et al. |
| 2015/0164336 | A1 | 6/2015 | Mahadevan-Jansen et al. |
| 2015/0247755 | A1 | 9/2015 | Pelletier et al. |
| 2015/0313533 | A1 | 11/2015 | Rapp et al. |
| 2016/0157757 | A1 | 6/2016 | Murthy |
| 2017/0003226 | A1 | 1/2017 | Parker |
| 2018/0042583 | A1 | 2/2018 | Pringle et al. |
| 2018/0045570 | A1 | 2/2018 | Smith et al. |
| 2018/0188117 | A1 | 7/2018 | Matousek et al. |
| 2018/0372540 | A1 | 12/2018 | Zhao et al. |

FOREIGN PATENT DOCUMENTS

| | | |
|---|---|---|
| WO | 2003/073082 A1 | 9/2003 |
| WO | 2006/061565 A1 | 6/2006 |
| WO | 2006/061566 A1 | 6/2006 |
| WO | 2007/113566 A2 | 10/2007 |
| WO | 2010/018557 A1 | 2/2010 |
| WO | 2011/065970 A1 | 6/2011 |
| WO | 2014/149071 A1 | 9/2014 |
| WO | 2017/001847 A1 | 1/2017 |

OTHER PUBLICATIONS

Bagavathiappan et al., "Infrared thermography for condition monitoring—A review," Infrared Physics & Technology 60, pp. 35-55 (2013).

Buckley et al., "Non-invasive analysis of turbid samples using deep Raman spectroscopy," Analyst, pp. 3039-3050 (2011).

Damaghi M. et al., "pH sensing and regulation in cancer," Frontiers in Physiology, No. 4, Art. 370 (2013).

Garg, R. et al., "Optical transmission in highly concentrated dispersions," Journal of the Optics Society of America A, vol. 15, pp. 932-935 (1998).

Hashim, A.I. et al., "Imaging pH and Metastasis," NMR Biomedical, vol. 24, No. 6, pp. 582-591 (2011).

Huang et al., "Plasmonic photo-thermal therapy (PPTT)," Alexandria Journal of Medicine, vol. 47, pp. 1-9 (2011).

Hynynen et al., "Temperature Monitoring in Fat with MRI," Magnetic Resonance in Medicine, 2000, vol. 43, pp. 901-904.

Jaworska, A. et al., "SERG-based monitoring of the intracellular pH in endothelial cells: the influence of the extracellular environment and tumour necrosis factor-α," Analyst, vol. 140, pp. 2321-2329 (2015).

Lahiri et al., "Medical applications of infrared thermography: A review," Infrared Physics & Technology, vol. 55, pp. 221-235 (2012).

Levick et al., "Validation of microwave radiometry for measuring the internal temperature profile of human tissue," Measurement of Science, vol. 22, pp. 1-8 (2011).

Maher et al., "Temperature-Dependent Anti-Stokes/Stokes Ratios under Surface-Enhanced Raman Scattering Conditions," Journal of Physical Chemistry, vol. 110, pp. 6797-6803 (2006).

Matousek, P. et al., "Numerical Simulations of Subsurface Probing in Diffusely Scattering Media Using Spatially Offset Raman Spectroscopy," Applied Spectroscopy, vol. 59, No. 12, pp. 1485-1492 (2005).

Matousek, P. et al., "Subsurface Probing in Diffusely Scattering Media Using Spatially Offset Raman Spectroscopy," Applied Spectroscopy, vol. 59, No. 4, pp. 393-400 (2005).

Matousek, P., "Inverse Spatially Offset Raman Spectroscopy for Deep Noninvasive Probing of Turbid Media," Applied Spectroscopy, vol. 60, No. 11, pp. 1341-1347 (2006).

Matousek, P. and Parker, A.W., "Bulk Raman Analysis of Pharmaceutical Tablets," Applied Spectroscopy, vol. 60, pp. 1353-1357 (2006).

Matousek et al., "Recent advances in the development of Raman spectroscopy for deep non-invasive medical diagnosis," Journal of Biophotonics, vol. 6, No. 1, pp. 7-19 (2013).

Pozzi et al., "Evaluating Single-Molecule Stokes and Anti-Stokes SERS for Nanoscale Thermometry," The Journal of Physical Chemistry, vol. 119, pp. 21116-21124 (2015).

Rindelaub, J.D. et al., "Direct Measurement of pH in Individual Particles via Raman Microspectroscopy and Variation in Acidity with Relative Humidity," Journal of Physical Chemistry A, vol. 120, pp. 911-917 (2016).

Schrader, B. and Bergmann, G., "Die Intensitat des Ramanspektrums polykristalliner Substanzen," Zeitschrift fur Analytische Chemie Fresenius, pp. 230-247 (1967). English summary.

Stone et al., "Surface enhanced spatially offset Raman spectroscopic (SESORS) imaging—the next dimension," Chemical Science, vol. 2, pp. 776-780 (2011).

Stone et al., "Prospects of Deep Raman Spectroscopy for Noninvasive Detection of Conjugated Surface Enhanced Resonance Raman Scattering Nanoparticles Buried within 25 mm of Mammalian Tissue," Analytical Chemistry, vol. 82, No. 10, pp. 3969-3973 (2010).

Vardaki, M.Z. et al., "Studying the distribution of deep Raman spectroscopy signals using liquid tissue phantoms with varying optical properties," Analyst, vol. 140, pp. 5112-5119 (2015).

Vo-Dinh et al., "SERS Nanosensors and Nanoreporters: Golden Opportunities in Biomedical Applications," Advanced Review, vol. 7, pp. 17-33 (2015).

Wang, F. et al., "Surface-Enhanced Raman Scattering Detection of pH with Silica-Encapsulated 4-Mercaptobenzoic Acid-Functionalized Silver Nanoparticles," Analytical Chemistry, vol. 84, pp. 8013-8019 (2012).

Search Report for Application No. GB1618260.2 dated Mar. 8, 2017.

International Search Report and the Written Opinion of the International Searching Authority for related International Application No. PCT/GB2016/051951, dated Sep. 6, 2016.

International Search Report and the Written Opinion of the International Searching Authority, for related International Application PCT/GB2017/053241, dated Feb. 9, 2018.

Schrader, B. and Bergmann, G., "Die Intensitat des Ramanspektrums polykristalliner Substanzen," Zeitschrift fur Analytische Chemie Fresenius, pp. 230-247 (1967). English summary.

Vo-Dinh et al., "SERS Nanosensors and Nanoreporters: Golden Opportunities in Biomedical Applications," WIRES Nanomed Nanobiotechnol 2015, 7:17-33. doi: 10.1002/wman.1283.

Jaworska, A. et al., "SERS-based monitoring of the intracellular pH in endothelial cells: the influence of the extracellular environment and tumour necrosis factor-α," Analyst, vol. 140, pp. 2321-2329 (2015).

International Search Report and the Written Opinion of the International Searching Authority, dated Feb. 9, 2018, from related International Application No. PCT/GB2017/053241 filed on Oct. 27, 2017.

(56) References Cited

OTHER PUBLICATIONS

Williams, Adam et al., "Multivariate spectral analysis of pH SERS probes for improved sensing capabilities: Spectral analysis of pH SERS probes," Journal of Raman Spectroscopy, vol. 47, No. 7, pp. 819-827, Jul. 1, 2016.

\* cited by examiner

DETECTION OF PH

STATEMENT REGARDING FEDERALLY SPONSORED RESEARCH OR DEVELOPMENT n/a

BACKGROUND OF THE INVENTION

The present invention relates to apparatus for non-invasive detection of pH, and to corresponding methods. More generally, the invention relates to methods and apparatus for measuring pH of a sub-surface volume of a sample, for example where the sample is diffusely scattering.

pH levels are important chemical and biological parameters for determining the nature or progress of chemical reactions in industrial, clinical and other areas. pH is usually measured electrically by direct contact of electrodes with a sample, for example by measuring the electrical potential between a reference electrode and a pH electrode, typically an ion selective doped glass electrode that is sensitive to hydrogen ions.

However, for many applications, direct contact with the sample is either undesirable, for example due to contamination risks, or not practical, for example because the part of the sample for which a pH measurement is desired does not present an exposed surface. Some such situations are clinical, for example where it would be desirable to measure the pH of tissue beneath the skin or within the eye of a human or animal subject. Other situations are industrial such as the desire to measure the pH of a fluid within a bioreactor without risk of contamination.

It would be desirable to provide methods and apparatus suitable for non-invasive detection of pH, for example for subcutaneous measurement of pH in a human or animal subject, and for other purposes.

BRIEF SUMMARY OF THE INVENTION

The invention provides for the sub-surface monitoring of pH levels in turbid media, that is in diffusely scattering samples, and enables non-invasive and sub-surface monitoring of pH, for example using embedded SERS nanoparticles with pH sensitive nanoparticle labels, using a technique of spatially offset Raman spectroscopy to overcome limitations of conventional Raman spectroscopy.

When we refer to determining or monitoring pH, this is to be taken as determining or monitoring any corresponding measure of acidity or alkalinity such as pOH.

More generally, the invention provides methods and apparatus for optical measurement of sub-surface pH of a sample. The pH may be derived for a plurality of depths or ranges of depth within a sample using techniques of spatially offset Raman spectroscopy, and may be determined without contact with the sample. In particular, the invention directs probe light to one or more first, entry regions on the sample surface, and collects the probe light, following scattering within the sample, from one or more second, collection regions some or all of which may be separate from and/or spaced from and/or spatially offset from the one or more entry regions. The collected light then contains spectral features arising from Raman scattering within the sample which can be analysed to determine one or more pH measurements at one or more depths or ranges of depth within the sample.

The pH can be determined by noting that particular Raman spectral features of molecules either natively present in the sample, or added as non-native reporter molecules, vary according to pH, for example in terms of intensity, wavelength, spectral shape and so forth.

Accordingly, the invention provides a method of measuring pH in a sub-surface volume of a sample, for example a diffusely scattering sample, comprising: directing probe light to an entry region on the sample surface; collecting said probe light from a collection region on the sample surface, following diffuse scattering within the sample, the collection region being spatially offset from the entry region; detecting one or more Raman spectral features in the collected probe light; and determining a pH of the sub-surface volume from the one or more Raman spectral features.

Determination of the pH may be at least partly from intensities of one or more of the detected Raman spectral features, and/or from spectral position (e.g. wavelength, wavenumber, frequency) of detected Raman features, and/or using numerical or statistical techniques to relate spectral features to a measurand such as principal component analysis.

Determining a pH of the sub-surface volume may comprise introducing reporter molecules into the sub-surface volume, detecting one or more Raman spectral features of the reporter molecules, and determining a pH of the sub-surface volume from the detected Raman features of the reporter molecules. Just one, or a plurality of different species of reporter molecules could be used in the same detection process.

Although the invention may be used for various different purposes, in some areas of application the sub-surface volume comprises tissue of a human or animal subject, and the reporter molecules are introduced into the sub-surface volume by being administered to the subject, for example by injection through the skin. In order to enhance the available spectral signal, for example to reduce the exposure time required to collect spectra with adequate signal to noise ratio or to minimise the required concentration of reporter molecules, the reporter molecules may be bound to nanoparticles to provide a surface enhanced Raman spectroscopy (SERS) effect for the detection of said one or more Raman spectral features.

The nanoparticles or other carrier mechanisms may be functionalised, typically by binding suitable functional groups or molecules to the nanoparticles or reporter molecules, so that these functional groups or molecules bind to specific targets of interest in the sample, for example to particular molecules or groups exhibited by tumour cells, such as surface proteins on target tumour cells. In this way, the reporter molecules can be caused to concentrate in regions of interest in a sample, such as in tumours or other target areas.

The method may comprise separately detecting said one or more Raman spectral features in the collected probe light for each of a plurality of different spatial offsets between said entry and collection regions. Because the path of scattering through the sample volume is on average deeper for wider spatial offsets, this technique provides depth information and enables associating the Raman features from each of said plurality of different spatial offsets with a different depth or distribution of depth within the sample, therefore also enabling a determination of a separate pH for each of one or more depths or distributions of depth within the sample.

The method may also comprise setting said entry and collection regions to be coincident or overlapping. In this case, the detected Raman spectral features are strongly biased in their origin towards the surface of the sample, typically approximately within or less than about one photon transport length of the surface (i.e. the distance over which the photon direction is just fully randomized). The Raman spectral features detected when the entry and collection regions are spatially offset may then be compensated for the unwanted (and often overwhelming) surface contribution using the Raman spectral features detected when the entry and collection regions are coincident or overlapping. Another use of this data is to determine a pH at the sample surface from the one or more Raman spectral features detected when the entry and collection regions are coincident or overlapping, using differences between the Stokes/anti Stokes features in the collected light.

The entry and collection regions may be shaped, spaced, offset and otherwise arranged and moved in a variety of ways. However, in some embodiments the entry region comprises one or more segments which are located around a centrally disposed collection region, for example as an annulus disposed around the collection region. Such arrangements provide for a relatively large entry region reducing the risk of damage through heating or burning by the probe light.

Irrespective of particular shape and arrangement, the entry and collection regions may typically be spatially offset by an offset by a distance in the range from 1 mm to 50 mm, and more preferably in the range from 3 mm to 20 mm. The optimum or chosen offset or range of offsets will depend on the sample. Embodiments of the invention may also make use of a null or zero offset between the entry and collection regions, in which the regions are coincident or overlapping, for example to provide a signal representative of the surface of the sample which can be used for subtraction, calibration or other compensation of signals obtained at non zero offsets.

Typically, the sample may be a diffusely scattering sample, or the sub-surface volume for which pH is determined may be diffusely scattering. In this case, the degree to which the sample or volume is diffusely scattering may be represented by photon transport length within the diffusely scattering region, which may typically be less than about 3 mm, say around 1 mm for human tissue, and in the region of around 0.1 to 1 mm for translucent plastics, pharmaceutical powders and tablets, body fluids such as blood and other turbid liquids or interest. For example, the sub-surface volume may be beneath the sample surface by least twice the diffuse scattering transport length of probe light in the sample, and/or the sub-surface volume may be at least 2 mm, or at least 5 mm, beneath the sample surface.

Although the entry and collection regions may be adjacent, proximal, or spaced apart on a surface which is largely planar or only moderately curved, thereby using a backscatter configuration, the entry and collection regions may also lie on parts of the surface with substantially different surface normal vectors, for example with normals in the region of 90 degrees apart, or even in the region of 180 degrees apart, and any angle or range in-between. For example, the entry and collection regions may be disposed on opposite or opposing sides of a sample, or such that a sub-surface volume the pH of which is being determined by the invention lies directly between the entry and collection regions. Such arrangements may be described as transmission configurations.

In such circumstances where the entry and collection regions are not substantially coplanar, a plurality of offsets between the entry and collection regions can still be used. For example, entry and collection regions may be arranged such that the local normals of the sample surface for the two regions takes on a range of different angle values, for example within the full range of 0 to 360 degrees around the sample.

Transmission arrangements in which material of the sample lies directly between the entry and collection regions may be of particular interest where the sample is small, for example being only of the order of about 5 mm to about 50 mm in diameter or thickness for strongly scattering samples, although larger diameters or spacings between entry and collection regions could be used for more transparent samples.

The sub-surface volume may comprises tissue of a human or animal subject, and the determined pH is then a sub-surface pH of the tissue. For example, the sample surface may be a surface of skin of the human or animal subject. In this context, the invention may be used to determine an indication of cancerous or infected tissue within the sub-surface volume from the determined pH.

Methods of the invention may be applied to a variety of other circumstances, for example to determine pH of a fluid within a containing wall, such as a fluid in a conduit or chamber. The entry and collection regions are then provided on said containing wall, for example on windows of the containing wall, and the sub-surface volume comprises a volume of the fluid. The chamber could be a chamber of a bioreactor or other vessel.

The invention also provides apparatus corresponding to the above methods, such as apparatus for measuring pH within a volume of a sample having a surface, comprising: a light source for generating probe light; delivery optics arranged to direct the probe light to an entry region on the surface; collection optics arranged to collect said probe light from a collection region on the surface, following scattering within the volume of the sample, the collection region being spatially offset from the entry region; a spectral analyser arranged to detect Raman spectral features in the collected probe light; and a processor arranged to determine a pH of the volume from the Raman spectral features.

The processor may be arranged to determine a pH of the volume from the Raman spectral features at least partly from one or more of intensities, spectral positions, and shapes of detected Raman spectral features. To enhance the available Raman signal indicative of pH, the volume may comprise reporter molecules, optionally using more than one such species of reporter molecule, and the processor may be arranged to determine pH from one or more Raman spectral features arising from the reporter molecules. For example, the reporter molecules may be bound to nanoparticles to provide a surface enhanced Raman spectroscopy (SERS) effect for the detection of said one or more Raman spectral features arising from the reporter molecules. Apparatus of the invention also includes such reporter molecules, and such nanoparticles, as discussed elsewhere in this document.

To enable multiple spatial offsets to be used, and therefore a depth profile of pH to be derived, the apparatus may comprise an offset driver arranged to provide a plurality of different spatial offsets between said entry and collection regions, the apparatus being arranged to separately detect said Raman spectral features for each different spatial offset, and to associate the Raman features from each of said plurality of different spatial offsets with a different depth or distribution of depths within the sample. The processor is then arranged to combine said Raman features from said different spatial offsets to determine a separate pH for each of one or more depths or distributions of depth within the sample. For example, a plurality of spatial offsets may be used in the range from 1 mm to 50 mm, and more preferably in the range from 3 mm to 20 mm, depending on the nature of the sample and the design of the apparatus. Zero or null spatial offsets or spacings, and transmission configurations of the entry and collection regions may also be used as already discussed above.

The processor may typically be implemented using one or more microprocessors with associated memory storing program instructions for carrying out the analysis of detected Raman spectral features as described herein, for the determination of pH, and optionally for determination of additional parameters such as chemical composition, temperature and so forth. The processor may also be used for suitable control of one or more of the light source, and the offset driver for setting the spatial offset between entry and collection regions, and may be connected to a display for displaying operational information of the apparatus and an input device for receiving operating instructions. The apparatus may also be arranged to display the determined pH or pH profile, for example on the display, or to output such information using a network or other data connection.

BRIEF DESCRIPTION OF THE DRAWINGS

Embodiments of the invention will now be described, by way of example only, with reference to the accompanying drawings, of which:

FIG. 10 shows how the invention may be applied to a bioreactor or similar;

DETAILED DESCRIPTION OF EMBODIMENTS

Figure 1:
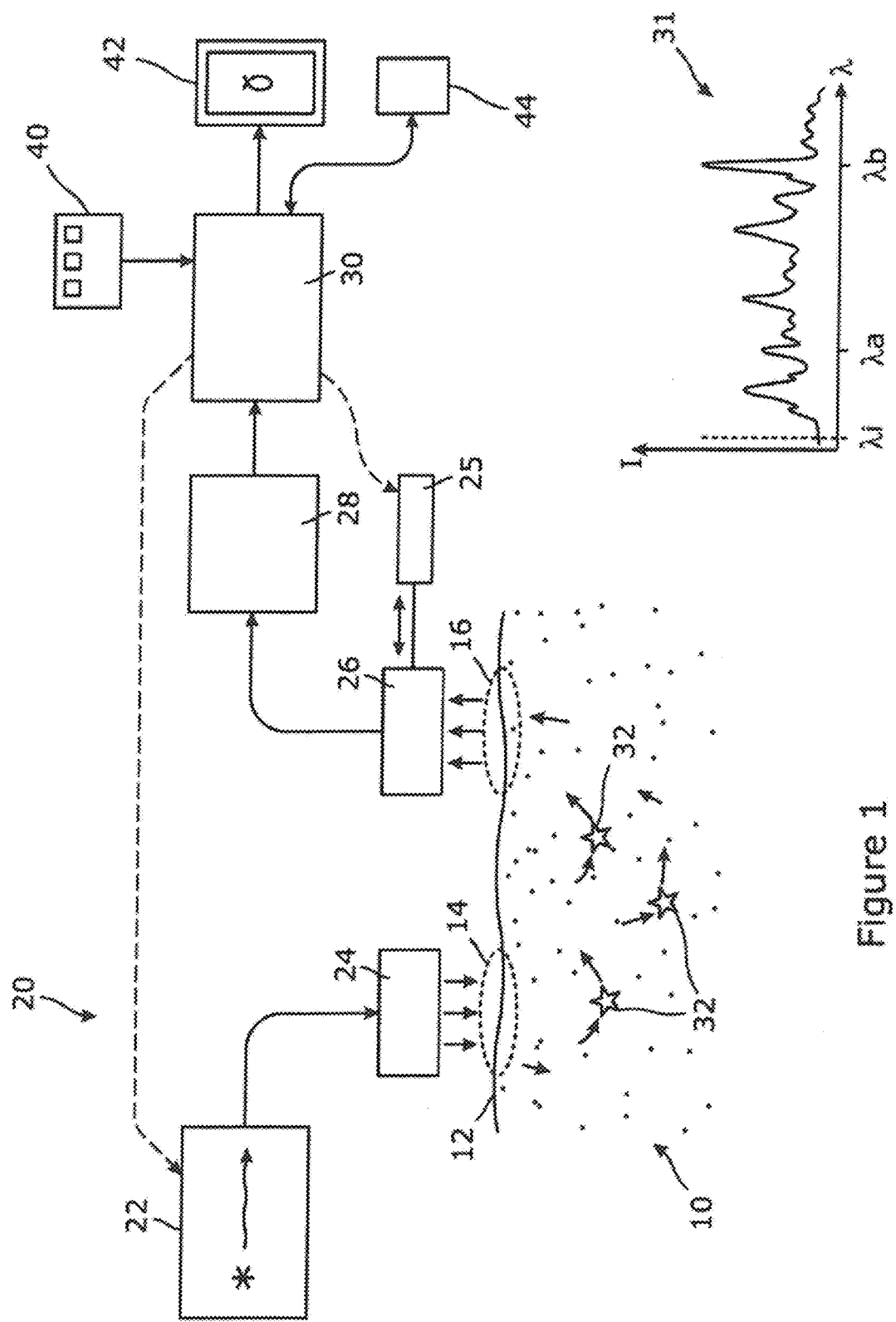
FIG. 1 schematically shows apparatus according to the invention for optically determining a pH in a sub-surface volume of a sample.

Referring now to FIG. 1 there is shown schematically apparatus 20 for measuring pH in a sub-surface volume of a diffusely scattering sample 10. The apparatus may be used for non-invasive detection of a sub-cutaneous or other sub-surface pH in a human or animal subject, in which case the sample 10 is body tissue of the subject, and the surface 12 of the sample may be defined as a surface of the skin of the patient or some other exposed membrane or surface such as the surface of the cornea or of surgically exposed tissue. Various other applications for the invention in determining sub surface pH of a sample, for example in industrial contexts, are discussed elsewhere in this document.

The apparatus comprises a light source 22 arranged to form a beam of probe light, and delivery optics 24 arranged to direct the beam of probe light to an entry region 14 on the surface 12 of the sample 10. Collection optics 26 are arranged to collect probe light, which has been scattered within the sample 10, from a collection region 16 spatially offset from the entry region 14. Optional relative movement of the entry and collection regions, to provide a plurality of offsets, may be provided by an offset driver mechanism 25, which may form part of or be combined with or be arranged to control the delivery optics and/or the collection optics.

A spectral analyser 28 then receives the collected light, and detects spectral features in the collected light which relate to scattering of the probe light within the sample. Data relating to the detected spectral features are then used by a processor 30 to determine pH of a sub-surface volume or region of the sample from the detected spectral features, as discussed further below. Using the optional offset driver, the apparatus may be arranged to separately detect Raman spectral features for each of a plurality of different offsets between the entry and collection regions, so as to provide a more depth selective determination of pH, and/or pH measurements at multiple depths.

The light source 22 may typically be a near infrared laser, emitting a beam of probe light in the near infrared region of the electromagnetic spectrum, for example at a wavelength of around 800 nm. The delivery optics 24 may be provided by one or more suitable optical fibres and/or lenses arranged to form the beam of probe light into a suitably configured entry region 14 on the surface of the sample. The collection optics 26 may also be provided by one or more suitable optical fibres and/or lenses to define the collection region 16 on the surface of the sample and to collected probe light from this region and deliver it to the spectral analyser 28. The spectral analyser 28 may be provided in various ways such as using a spectrometer such as a dispersive spectrometer, or by suitable optical filters in combination with photodetectors, or in other ways, in order to detect particular spectral features in the collected light.

Aspects of the spectral features detected by the spectral analyser 28 are illustrated in FIG. 1 at graph 31. In this graph, the wavelength of the probe light generated by the light source 22 is depicted as $\lambda_i$. Typically, this wavelength of light may be suppressed or substantially removed by the collection optics 26, before the collected light is received by the spectral analyser 28, for example using a suitable optical filter, so that there is no corresponding central peak shown in the graph 31. In order to determine a pH of a sub-surface volume of the sample from the detected spectral features, the detected spectral features include Raman spectral features resulting from Raman scattering within the sample 10. Such scattering events are shown in FIG. 1 by reference numeral 32.

The processor 30 may also be used to provide control and/or monitoring of other elements of the apparatus, for example of the light source 22 and the offset driver 25. An input 40 may be used to provide user input or control instructions to the apparatus by connection to the processor, and a display 42 may be used by the apparatus to output operational information. The determined pH(s) or pH profile(s) may also be presented to a user on the display 42, and/or output to another entity using a data connection 44. Of course, the input 40 and display 42 could be combined into a single touch screen display if desired.

Many chemical species which may be natively present or introduced into the sample exhibit Raman spectral features with characteristics which change according to the local pH in the vicinity of the species. Typically, such a species may exhibit one or more spectral features which change in one or more of intensity, position, and shape according to the local pH. Methods of determining pH from such features may then include, for example:

- comparing the intensity of two such features such as peaks $2\backslash\lambda_a$ and $\lambda_b$ shown in FIG. 1, and deriving the pH from a known relationship with that comparison, for example from a difference or more particularly a ratio between the intensities;
- determining a wavelength or wavenumber shift in one or more features such as spectral peaks;
- detecting the shape or structure of one or more Raman spectral features or a waveband;
- analysis methods such as principal component analysis which combine such techniques as the above into a parameterised determination of a desired measurand from a set of experimental or theoretical spectra.

In other words, calibrating the optical response of a species to pH may involve ratiometric analysis of two strong Raman modes, and determining how this ratio evolves as a function of pH, or may involve various other simpler or more complex procedures, but in any case relies on Raman spectral features measured using apparatus such as that of FIG. 1 being sensitive to pH in a deterministic manner.

Most organic tissue offers some ability to monitor pH because constituent molecules such as amino acids, sugars and DNA are protonation sensitive molecules, and industrial chemical and other processes may also include the use of protonation sensitive molecules. However, in many circumstances the pH signal available from Raman spectral features arising from chemical species natively found in the sample will be small except under very large changes in pH.

Embodiments of the invention therefore typically make use of one or more species of reporter molecules which are selected for the sensitivity of one or more Raman spectral features to changes in pH. These reporter molecules are introduced into the sample, and in particular at least into the sub-surface volume where pH is to be detected. This introduction of reporter molecules may be achieved in various ways. In the case of a human or animal subject the reported molecules may typically be injected into the sub-surface volume. In the case of an industrial process of manufacture or monitoring, the reporter molecules may be mixed with the material which is to form the sub-surface volume during monitoring or testing, whether that is a solid, liquid, or other phase or mixture of phases at the time of monitoring or testing according to the invention.

The sensitivity of one or more Raman spectral features of the reporter molecules to changes in pH may be substantially enhanced in various ways in order to achieve a stronger pH signal. For example, the reporter molecules may be bound to the surfaces of nanoparticles to provide a surface enhanced Raman spectroscopy effect (SERS). In SERS techniques the intensity of the Raman signal is enhanced by up to many orders of magnitude, for example by the action of plasmonic resonances. Such enhancement is typically achieved by using nanoparticles of an appropriate size which are formed from noble metals such as gold, silver or platinum.

The use of reporter molecules bound to nanoparticles to achieve Raman detection of pH changes is discussed for example in Williams et al., *Journal of Raman Spectroscopy*, 2016, 47, 819-827, Wang et al., *Analytical Chemistry*, 2012, 84, 8013-8019, Rindelaub et al., *Journal of Physical Chemistry A*, 2016, 120, 911-917, and Jaworska et al., *Analyst*, 2015, 140, 2321-2329, the contents of which are hereby incorporated by reference. Some specific reporter molecules which can be used to detect pH from Raman spectral features include 4-mercaptopyridine, 2-aminothiophenal, 4-aminothiophenol, 2,5-dimercaptobenzoic acid, 3,5-dimercaptobenzoic acid, and para-mercaptobenzoic acid (pMBA). Techniques for binding suitable reporter molecules to suitably prepared nanoparticles for carrying out SERS techniques are found in the above references and elsewhere in the prior art. The reporter molecules on the nanoparticles then provide the pH sensitive Raman signal, and the nanoparticles provide enhancement of that Raman signal to improve detection.

The processor 30 therefore preferably determines pH of a sub-surface volume of the sample 10 using detected properties, such as intensities, of two or more detected Raman spectral features. The pH may be determined using one or more ratios of the intensities of a particular set of two or more features. For example, a detected Raman spectrum will typically contain a large number of Raman spectral features, which may arise from one or a plurality of chemical species, and the determination of pH may make use of a plurality of such features, for example taking ratios of particular pairs of features and combining the ratios.

If the reporter molecules are bound to nanoparticles, for example to achieve the SERS enhancements discussed above, then these nanoparticles may also be functionalised with anti-bodies or other species so that the nanoparticles bind to specific molecular targets of interest in the sample, for example to tumour tissue in a human or animal subject.

The proportion of scattering of the probe light within the sample which is inelastic Raman scattering, compared with the proportion of scattering which is elastic scattering is typically very small, usually with a difference of many orders of magnitude, even when SERS techniques discussed above are used, and especially when the sample is highly scattering as is typically the case with human tissue and many other application areas. As a consequence, most photons of probe light are not Raman scattered in a diffusely scattering sample. However, each photon of probe light which is Raman scattered within the sample is also subsequently scattered elastically a large number of times, giving rise to a random walk of the photon through the sample. The average path of this random walk through the sub-surface volume of the sample, between the entry region and the collection region, depends on the spatial offset between these regions. It can be seen that for larger spatial offsets the average depth of the path will be deeper within the sample.

Using this principle, the spacing between the entry and collection regions can be controlled or adjusted by the apparatus 20 in order to control the distribution of depths at which the Raman scattering occurs. This technique is referred to as spatially offset Raman spectroscopy (SORS), and is discussed in detail in WO2006/061565 and WO2006/061566, the contents of which are incorporated herein by reference for all purposes, including for illustrating how characteristics of the sample may be determined at particular depths and profiles of depth within the sample. According to the present invention, such characteristics may include pH within the sample. Some ways in which Raman spectral features or related information from different spatial offsets may be combined to derive characteristics of the sample selected for one or more depths or one or more profiles of depths, are discussed in the above patent publications, but may include simple subtraction schemes for example in which the spectral features for a small or null offset are subtracted from those of one or more larger offsets, or more complex multivariate analysis, such as principle component analysis in which statistical relationships between detected spectral features at multiple offsets are used to derive pH at a depth, profile of depth, or multiple such depths or profiles of depth. According to the principles of spatially offset Raman spectroscopy, therefore, the entry and collection regions may be of various sizes and shapes, and for any particular spatial offset these regions may each be formed by single contiguous or multiple discrete segments on the surface of the sample. Some examples of such regions are depicted in FIGS. 2a and 2b.

Figure 2A:
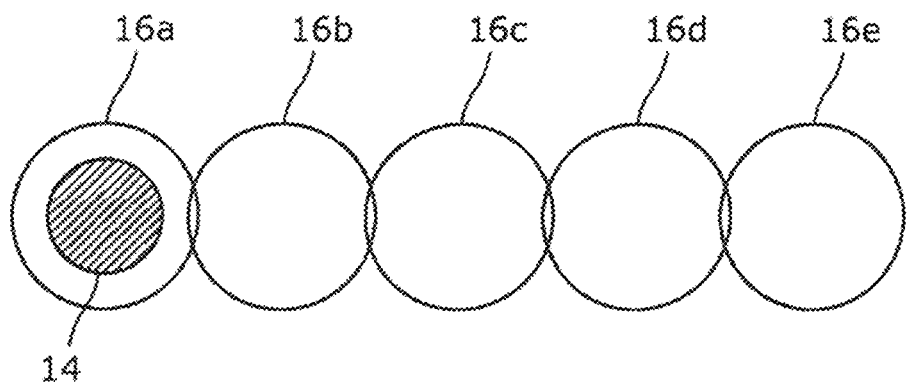
FIGS. 2a and 2b show some configurations for spaced probe light entry and collection regions into the sample.

In FIG. 2a, an entry region 14 is provided at a fixed position, and multiple collection regions 16a-16d are provided at increasing spatial offsets from the single entry region. Optionally, one of the illustrated collection regions 16a is coincident with, or overlapping with the entry region 14, so as to form a zero offset or null spacing. This zero offset can conveniently provide a signal representative of the surface of the sample, for compensating signals derived from larger signals. This can be done, for example, by subtracting Raman features detected for the null spacing from Raman features detected for one or more larger spacings.

Using the arrangement of FIG. 2a as an illustration, it will be seen that any number of spatial offsets between the entry and collection regions may be used, for example from one up to ten or more offsets, with Raman features typically being detected during separate exposure time intervals for each offset. Although in FIG. 2a the entry region remains fixed relative to the sample and the collection region is moved, the entry region could be moved instead or as well as the collection region. The regions in FIG. 2a are essentially circular or elliptical in shape, typically determined by convenience of implementation of the delivery and collection optics, various other shapes may be used. In FIG. 2a none of the collection regions 16b-16d overlaps with the entry region, but some overlap maybe permitted.

Figure 2B:
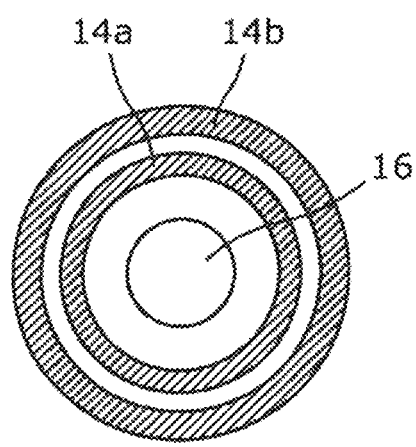

In FIG. 2b, a concentric arrangement is used in which a central collection region 16 lies within a surrounding entry region 14a, which could be in the form of a continuous or broken annulus. This has an advantage in that the entry region is relatively large, and therefore can be provided using a lower intensity of illumination to avoid damaging the sample. Multiple spatial offsets can then be provided by varying the radius of the entry region, as depicted by concentric entry regions 14a and 14b.

In order to provide sufficient scattering of the probe light to be able to detect Raman spectral features originating at depth with the sample, the sample may be diffusely scattering or turbid or strongly diffusing. The degree of such scattering will depend on the sample, and may be defined in terms of transport length which is a length over which the direction of propagation of photon of probe light is randomized. The skilled person knows that transport length l* of diffusive scattering may be taken as being related to the mean free path by the expression:

$$l^* = \frac{l}{1-g}$$

where g is the asymmetry coefficient (average of the scattering angle over a large number of scattering events), and l is the mean free path. The diffuse scattering transport length for samples suitable for use with the present invention may be of the order of 1 mm for human or animal tissue, of the order of 100 μm for powders such as those from which pharmaceutical tablets are comprised, a few times 100 μm for uPVC materials and similar plastics, and so forth. To this end, the invention may apply to samples and volumes of samples in which the transport length is less than about 3 mm, or less than about 0.3 mm To this end, the invention may typically therefore be used with one or more spatial offsets between the entry and collection regions ranging from about 1 mm to about 50 mm, and more typically from about 3 mm to about 20 mm, and for determining pH at depths within the sample of in the range from about 1 mm to about 30 mm and more typically from about 2 mm to about 15 mm. Embodiments of the invention may be arranged to determine pH at just one depth or depth profile, for example using a single spatial offset between the entry and collection regions, or may be arranged to determine pH at each of multiple depths or depth profiles. Embodiments may also use a zero or null offset in order to determine a pH at the surface of the sample FIGS. 1, 2A and 2B depict entry and collection regions which are adjacent, proximal, or spaced apart on a surface which is largely planar or only moderately curved. Such an arrangement may be described as a backscatter configuration, because after penetrating into the sample and undergoing Raman scattering in a sub-surface region, a photon of probe light is backscattered to the surface of the sample for collection by the collection optics. However, the entry and collection regions may also lie on parts of the surface which are far from coplanar, with substantially different surface normals, for example with normals in the region of 90 degrees apart, or even in the region of 180 degrees apart, or any other angle or range of angles.

Figure 3:
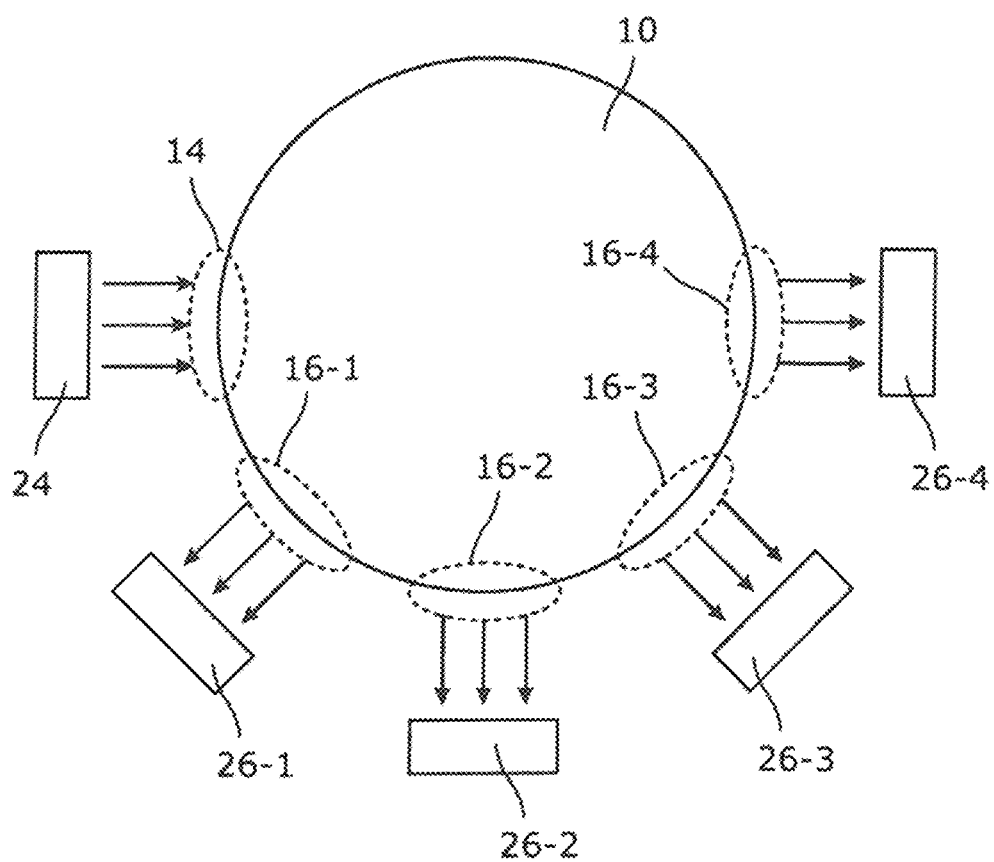
FIG. 3 shows how entry and collection regions may be disposed at different positions around a sample, for example in one or more transmission configurations.

For example, the entry and collection regions may be disposed on opposite sides of a sample, or such that a sub-surface volume the pH of which is being determined by the invention lies directly between the entry and collection regions, and such arrangements may be described as transmission configurations. An example of a transmission configuration is provided in FIG. 3. In this figure, delivery optics 14 define an entry region 14 on one side of a sample 10. Four different positions for collection optics 26-1-26-4 are then shown in the figure to form four different collection regions 16-1-16-4. The collection region 16-4 is on an opposite side of the sample 10 from the entry region, whereas the other collection regions 16-1-16-3 are spaced at angles of about 45, 90 and 135 degrees about the sample from the entry region. In such an arrangement, just one entry and one collection region could be used, or either or both or multiple entry and multiple collection regions may be used.

Transmission arrangements in which material of the sample lies directly between the entry and collection regions may be of particular interest where the sample is small, for example being only of the order of about 5 mm to about 50 mm in diameter or thickness for strongly scattering samples, although larger diameters or spacings between entry and collection regions could be used for more transparent samples.

Further discussion of transmission geometries and other details of such arrangements which can be used in embodiments of the present invention, to determine pH of a sub-surface region of a sample, can be found in the prior art including WO2007/113566, the contents of which is incorporated herein by reference in its entirety, to demonstrate how to arrange suitable transmission geometries for use in the present invention, and for all other purposes.

The principle of spatially offset Raman spectroscopy is based upon the concept that when Raman spectra of diffusely scattering media are collected at a location that is separated by a distance Δs from the laser illumination, the signal generated contains contributions from the materials buried beneath the surface of the material being probed. The larger the value of Δs the larger the relative contribution of the signals from the buried regions of the sample. However, the principle of detecting pH from a sub-surface volume of a sample using Raman spectroscopy can also be demonstrated using a transmission geometry where the entry region is on an opposite side of the diffusely scattering sample from the collection region.

Figure 4:
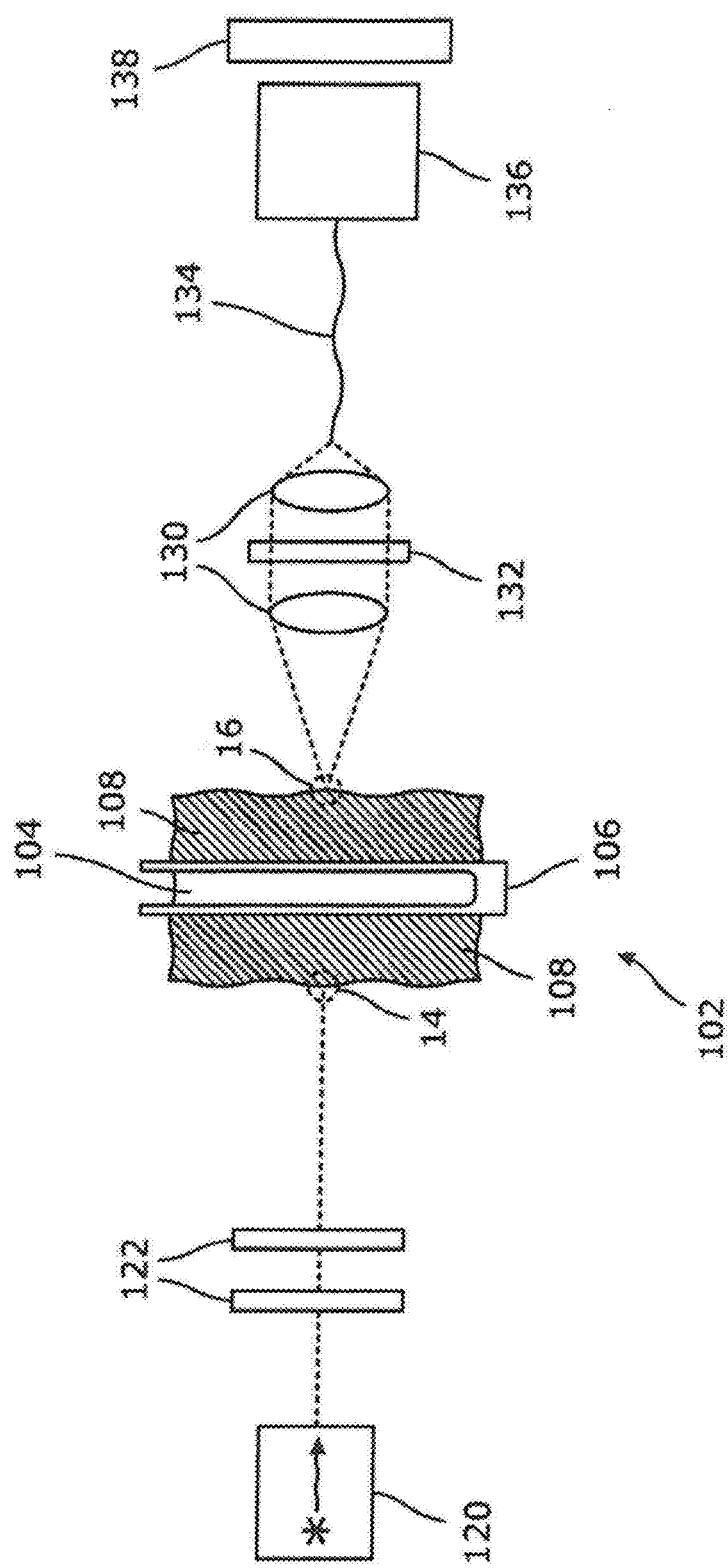
FIG. 4 shows an experimental arrangement for demonstrating the invention.

To this end, FIG. 4 presents a schematic diagram of an experimental setup used to demonstrate the present invention for pH measurements in a sub surface volume of a sample. The sample 102 of FIG. 4 is provided by a solution of prepared SERS nanoparticles 104 placed in a quartz cell 106 with opposing walls each about 1 mm thick, and a 2 mm optical path length between the walls through the nanoparticle solution. A layer of porcine tissue 108 each about 7.5 mm in thickness is provided on each outside wall of the quartz cell, so that the total thickness of the sample between the outside surfaces of the porcine tissue 108 is about 19 mm.

SERS nanoparticles were produced using the method described in Jaworska et al., *Analyst,* 2015, 140, 2321-2329, the contents of which are hereby incorporated by reference. 1 ml of 0.05 mg/ml gold nanoparticles with 100 nm nominal diameter (obtained from nanoComposix in San Diego, USA) was mixed for five minutes with reporter molecules provided by 100 µl of 1 nM 4-Mercaptobenzoic acid (MBA), so that reporter molecules became bound to the nanoparticles. Following mixing, the sample was centrifuged at 3000 rpm for 10 minutes, the supernatant was removed, and the prepared SERS nanoparticles were re-suspended in 1 ml of phosphate buffered saline (PBS) solution.

The optics of FIG. 4 were arranged to provide an entry region 14 and a collection region 16 at opposite sides of the sample, on the outside surfaces of the porcine tissue 108. An optical source 120 was provided by a spectrum stabilised laser (Innovative Photonic Solutions I0830MM0350MF-EM) with an excitation wavelength of 830 nm in combination with two 830 nm band pass filters 122 to provide a cleaner probe light spectrum. The collection optics were provided by a matched pair of lenses 130, a notch filter 132 to exclude the excitation wavelength, and a fibre optic bundle 134 to guide the collected probe light to a spectral analyser comprising a Kaiser spectrometer 136 (Holospec 1.8i) using a deep depletion CCD camera 138 (Andor iDus-420) to collect the Raman spectra.

Each Raman spectrum was collected over a total exposure time of 1800 seconds. The experiment was first carried out with the porcine tissue layers absent, with the resuspended SERS nanoparticles at an approximately neutral pH and then at a high pH of about 12 following addition of concentrated sodium hydroxide.

Figure 5:
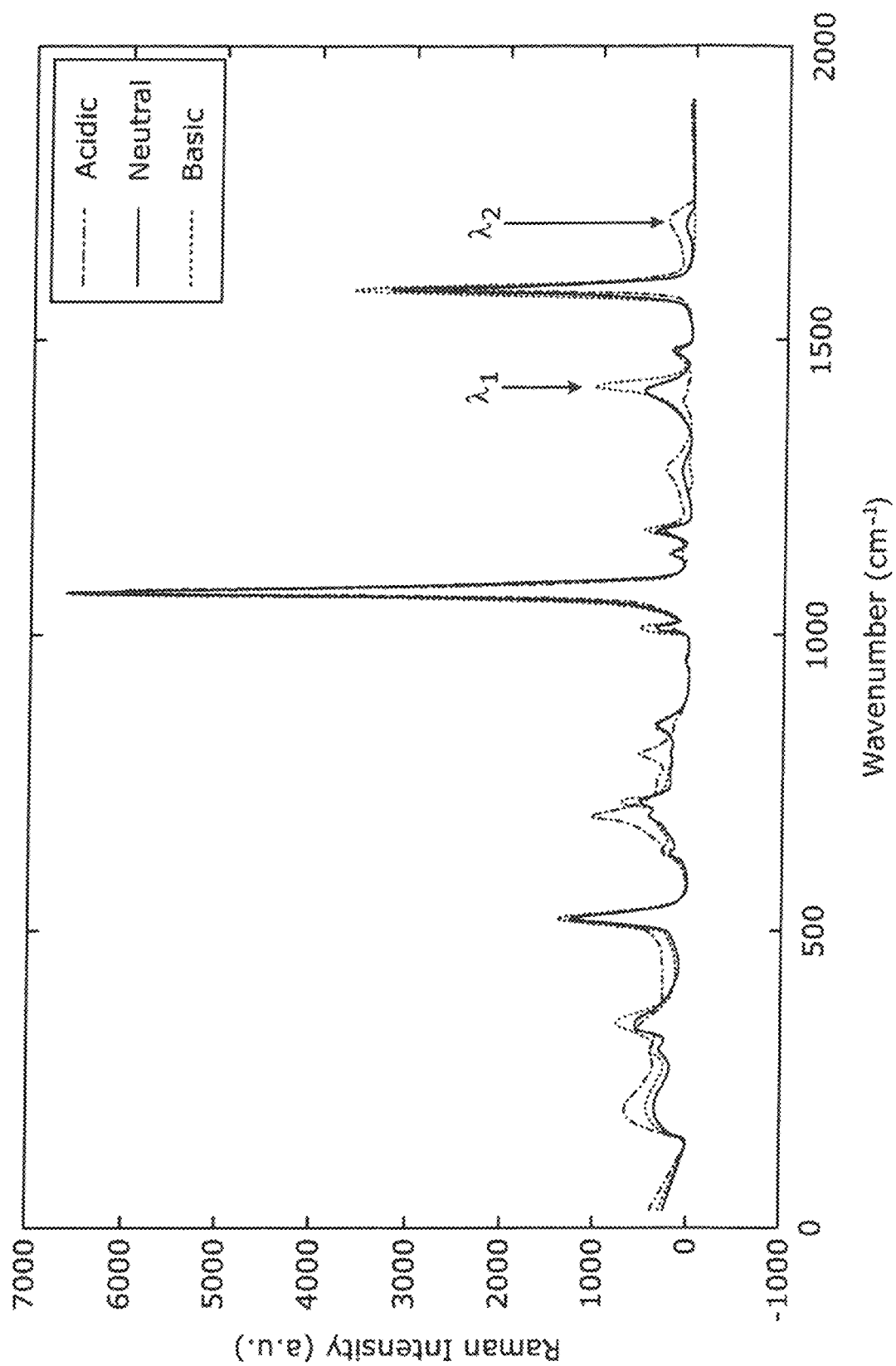
FIG. 5 illustrates Raman spectra of MBA reporter molecules bound to SERS nanoparticles for neutral and basic pH conditions using the arrangement of FIG. 4 but without the presence of porcine tissue layers.

FIG. 5 shows Raman spectra determined using the above arrangement with the porcine tissue layers absent, separately at neutral pH and then at an elevated pH of about 12 and a lowered pH to provide acidic conditions. Although two particular Raman bands shown as $\lambda_1$ and $\lambda_2$ which are sensitive to pH are quite weak compared with some of the other Raman bands of the MBA reporter molecule, a clear change is seen between the different pH levels for both bands.

Figure 6:
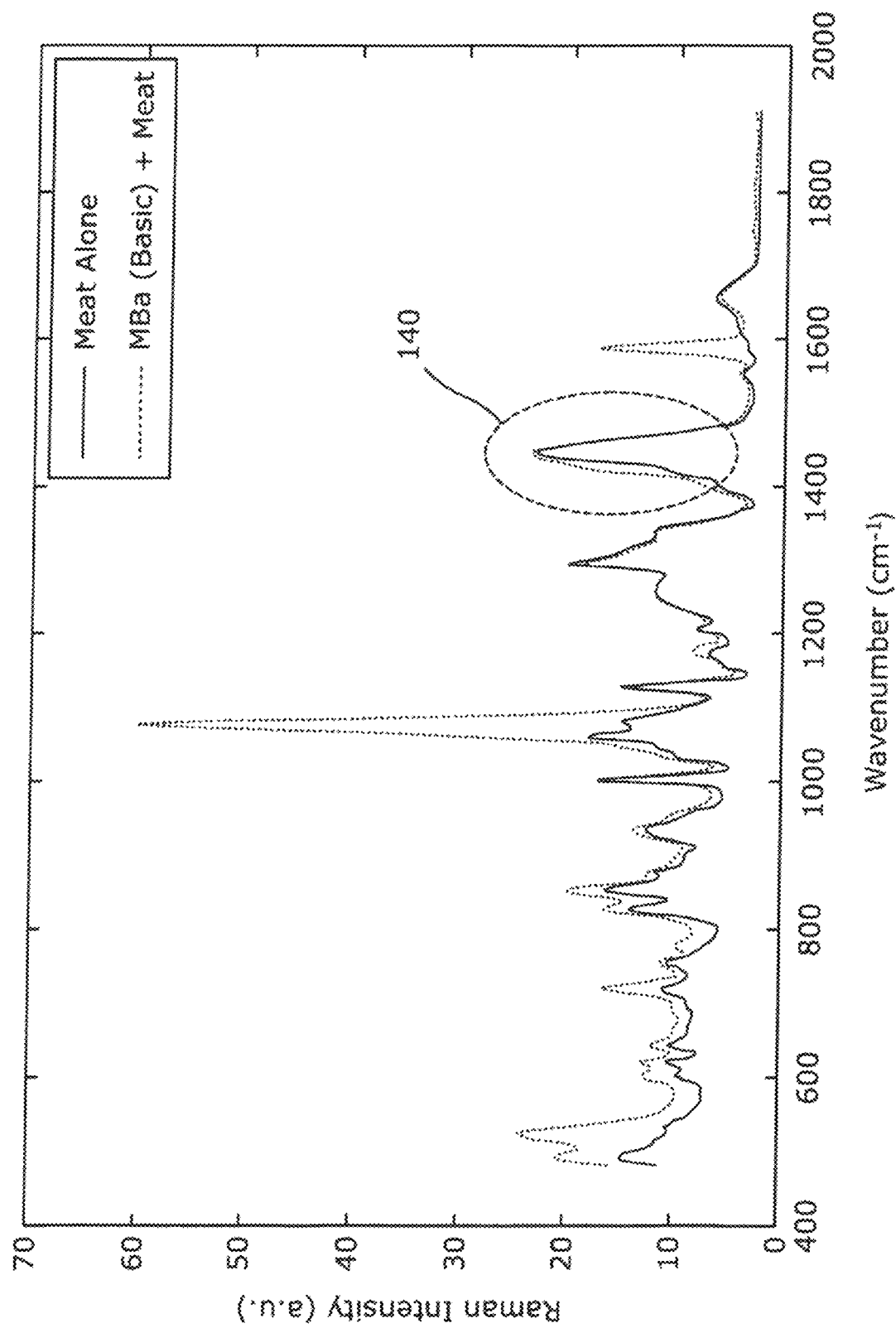
FIG. 6 is a graph of Raman spectra measured using the arrangement of FIG. 4, both with and without the porcine tissue layers, for neutral pH.

FIG. 6 shows results of a similar experiment, but with the porcine tissue in place in the sample 102 around the quartz cell. The broken curve then depicts the Raman spectrum with the quartz cell empty, and the solid curve with the re-suspended prepared nanoparticle solution in the quartz cell. The region labelled 140 illustrates a region of the spectrum which is particularly relevant for pH detection, corresponding to Raman band $\lambda_1$ shown in FIG. 5. However, it can be seem that overlap between the Raman signature of the porcine tissue with that of the reporter molecules introduces a potential error into the measurement of pH using this method. This could be dealt with in various ways, for example by spectral demixing using multivariate analysis, or Raman features less affected by overlap with tissue features may be used.

Figure 7:
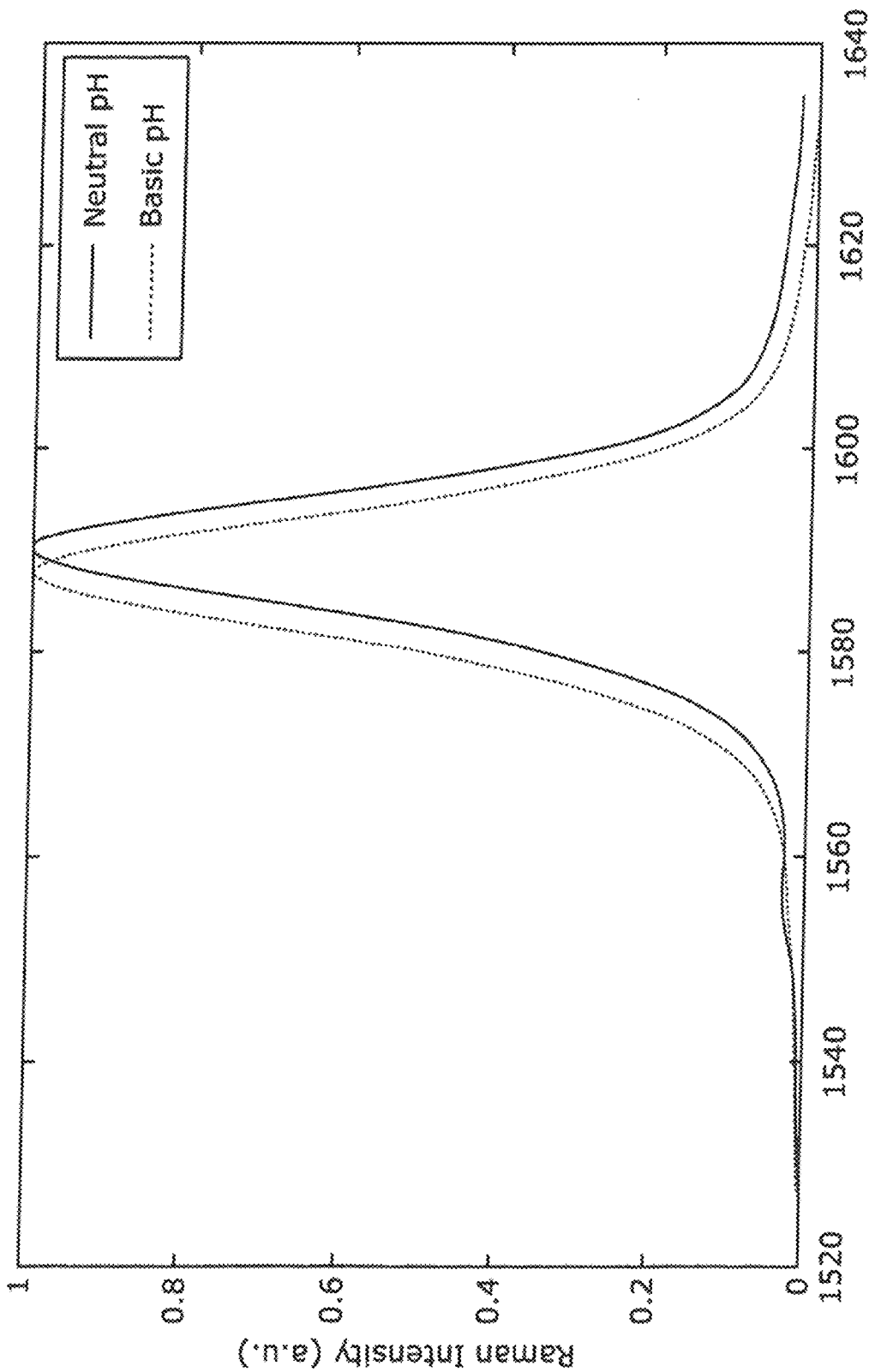
FIG. 7 shows a change in position of a Raman spectral feature of the MBA reporter molecules under a change in pH from neutral to basic.

FIG. 7 therefore shows results of a similar experiment, but with the graph showing only the waveband feature around 1590 to 1610 cm$^{-1}$, and without porcine tissue being present around the quartz cell 106. As can be seen from FIG. 6, this band does not significantly overlap with any strong Raman signal from the porcine tissue, so that it can be used for detecting pH more easily without further correction. In particular, the figure shows a significant downward shift in wavenumber by about 5 cm$^{-1}$ with the increase in pH from neutral to basic (a pH of about 12 was used). For this particular Raman band, the pH can be determined from the wavenumber position of the illustrated peak, and demonstrates the possiblity of using the position of a non-overlapping Raman band of the reporter molecules as a pH monitor.

Although in FIG. 7 a Raman feature is shown which demonstrates a shift in wavenumber with pH, a pH signal can be determined from various other behaviours of Raman spectral features. For example, such spectral features may increase or decrease in intensity, change shape, become broader or narrower, and may display a combination of such changes as pH changes. The relationship between the Raman spectral features and pH can be characterised and analysed in various ways, for example by ratiometric analysis of the magnitudes of spectral features, through the determination of shifts in wavenumber (or equivalently wavelength or frequency) of spectral features, and more generally by statistical or numerical analysis techniques for example multivariate analysis techniques such as principle component analysis, for example as discussed in Williams et al., *Journal of Raman Spectroscopy,* 2016, 47, 819-827.

In the text above, the invention has been discussed both in general terms and in terms of detection of pH in sub-surface tissue of a human or animal subject. Further discussion of clinical areas, and of a variety of other areas of application of the invention will now also be presented.

The detection of pH in human and animal subjects may be used for a variety of purposes. Cancerous tumour cell tissue is known to exhibit differences in pH from corresponding healthy tissue, for example see Damaghi M, Wojtkowiak J W and Gillies R J (2013) "pH sensing and regulation in cancer", Frontiers in Physiology volume 4, article 370, and Hashim A. I. et al., "Imaging pH and Metastasis", NMR Biomed. 2011 July; 24(6): 582-591. In particular, such tumour tissue frequently exhibits lowered pH levels, and embodiments of the invention may therefore be used as a tool to provide an indication of such cancerous tissue or lesions within a subcutaneous tissue without surgical intervention. Typically in this situation the skin of the patient will form the sample surface referred to above, but a surgically exposed tissue may instead provide the surface. Such embodiments of the invention may particularly be used to detect near surface cancers such as skin cancers. To enhance the detection process, SERS nanoparticles carrying the reporter molecules may be injected into sub-surface tissue to be investigated, or may be injected into the lymphatic or vascular system. Such nanoparticles may also be bound to molecules which provide the function of binding to specific molecules of interest, such as surface proteins found in particular cancer cells.

Other medical areas where the invention may be used include the monitoring of wound healing and infections, the detection of pH in blood, lymph, the eye, and other tissues.

Figure 8:
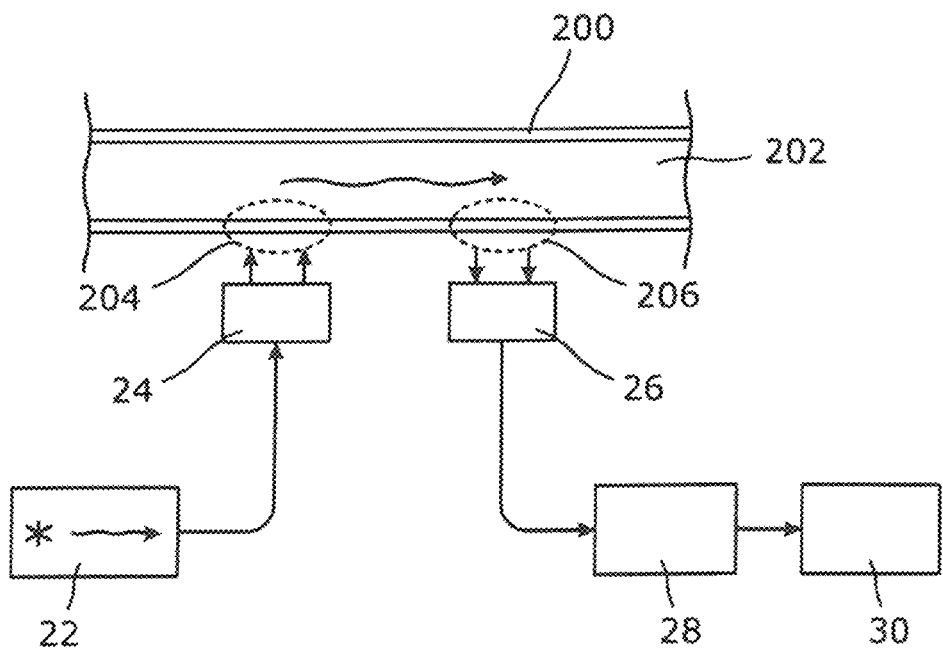
FIGS. 8 and 9 show how the invention may be applied to a conduit or other vessel containing a fluid.

Embodiments of the invention may also be used in various medical areas involving pH of samples outside the body. FIG. 8 illustrates a conduit 200 such as a pipe or tube along which a diffusely scattering fluid 202 is flowing, typically but not necessarily comprising a suspension of particles within a liquid. The conduit 200 is transparent or translucent to probe light delivered to an entry region 204 on a surface of the conduit by suitable delivery optics 24, such that the probe light at least partly passes through the conduit 200 and into the fluid, where Raman scattering of the probe light takes place. Scattered probe light passes out of the fluid 202 through the conduit, passing through a collection region 206 to be collected by collection optics 26 such that the entry region 204 is spaced from the collection region 206. Multiple spacings between the entry and collection regions may be used if required as already described above. Instead of the conduit 200 as a whole being transparent or translucent, the conduit 200 may be provided with one or more suitable windows transparent or translucent to the probe light, upon which the entry and collection regions may be formed.

FIG. 8 also shows a probe light source 22, a spectral analyser 28 and a processor 30 as already described in respect of earlier figures. The spectral analyser 28 detects Raman features and the processor 30 uses these features to determine a pH of the fluid 202 within the conduit 200.

Figure 9:
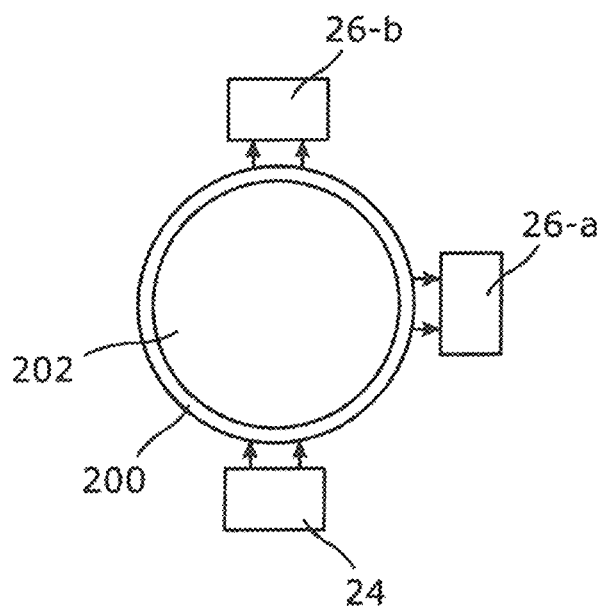

Although the entry and collection regions of FIG. 8 are shown as being spaced along an axial direction of the conduit, they may be spaced in other ways for example as shown in FIG. 9, where a first example collection region 26-a is shown spaced at a first angular offset in respect of the conduit axis (in this case at 90 degrees), and a second example collection region 26-b is shown spaced at a second angular offset (in this case at 180 degrees).

Arrangements such as those shown in FIGS. 8 and 9 may be used in a variety of medical applications where fluids are to be processed outside the body, and pH of those fluids needs to be monitored. pH measurement using the present invention has the advantage of not requiring any contact with the fluid 202 in the conduit, thereby avoiding risk of contamination. Moreover, the depth within the conduit 200 at which the fluid pH is monitored can be adjusted or varied by controlling the spatial offset between and other properties of the entry and collection regions. To this end, the conduit 200 may form part of, for example, a transfusion system, an IV warming system, a dialysis system, a cardio-pulmonary bypass system, and ECMO system, or a blood analyser. The fluid 202 in the conduit could therefore be blood or blood components, fluid to be administered intravenously, etc.

In some embodiments, the conduit 200 could instead be a vessel or container within which a fluid (such as blood or a fluid for intravenous use) is to be contained, and the invention may then be used to determine a pH of the fluid in the same way.

Figure 10:
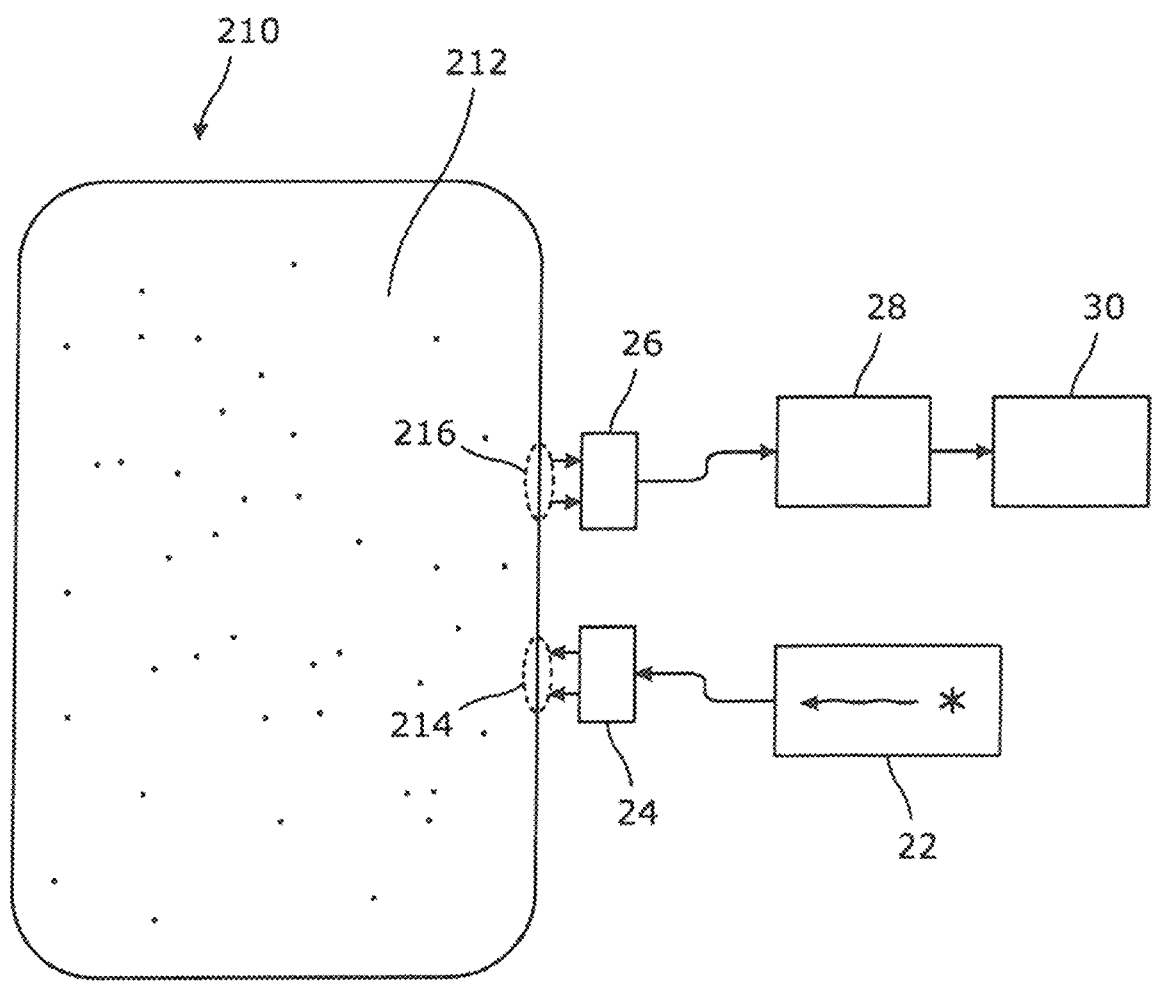

The invention may also be used to provide non-invasive pH measurement of reagent fluids contained within bioreactors, thereby providing detection of pH at depth within the reagent fluids without risk of contamination. To this end, FIG. 10 illustrates schematically a bioreactor 210 containing reagents 212 retained within a vessel wall 213. Apparatus as described elsewhere in this document is provided to determine a pH of the reagents, by providing an entry region 214 and a collection region 216 on the vessel wall. For example, the vessel wall may be transparent or translucent, or the entry and collection regions may be provided on suitable windows in the vessel wall.

The bioreactor 210 may be, for example, a stirred tank reactor, an airlift reactor, a packed bed reactor, a fluidised bed reactor, a photobioreactor, a membrane bioreactor, a rotary drum reactor, and/or a single use bioreactor, part of a rocking motion or stirred tank system, or any vessel system/configuration that supports a biologically active environment.

Bags and single-use bioreactors are in the process of revolutionising the way biopharmaceuticals are manufactured. Since its introduction more than 10 years ago, single use bioreactor technology has now become an established addition to today's biotechnology manufacturing facility. Many single use options are available, each with its advantages and disadvantages, although scalability is often promoted as one of the biggest general limitations. One of the biggest advantages of single use bioreactors is flexibility. The increasing trend towards multi drug facilities demands the production of different drugs using the same facility, with minimum time and cost, without compromising the quality of the drug. The development of robust and accurate single use sensor technologies will speed up the adoption of fully single-use bioreactors. Wave induced motion SUBs form the largest segment of the SUB market. Biologics manufacturing is expected to be the fastest-growing end-user segment for this market.

Embodiments of the invention may also be used in food processing such as dough mixing, microwave heating, frozen food products, baking and so forth, to remotely detect sub surface pH of a food product or food component without risk of contamination. For example, measuring the pH of bread and pastry dough while mixing is difficult at best with conventional electrical contact pH meters, due to breakage and possible contamination of the food. However, the pH is quite important in the production process. To this end, the sample illustrated in FIG. 1 may be a food product or component, and such a product or component may be contained within a suitable vessel, conduit or other container as illustrated in FIGS. 8, 9 and 10 and in other ways.

Figure 11:
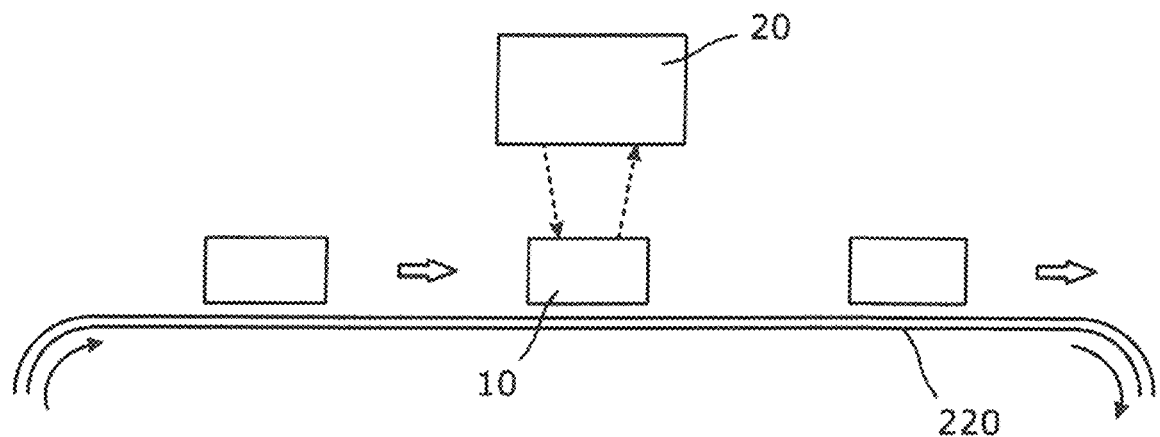
FIG. 11 shows the invention applied to detecting sub-surface pH of moving sample objects, for example along a conveyor.
Figure 12:
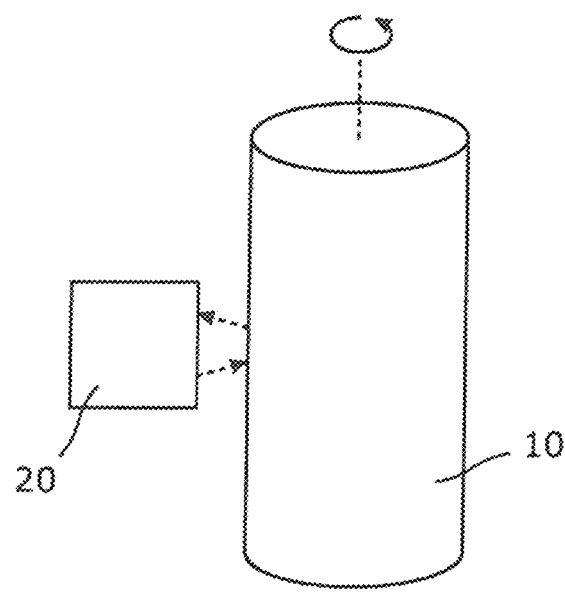
FIG. 12 shows the invention applied to detecting sub-surface pH of a rotating object.

FIG. 11 shows how apparatus 20 for measuring pH in a sub-surface volume of a sample 10 may be provided to determine sub-surface pH in a plurality of sample objects 10 moving relative to the apparatus, for example being carried along a conveyor 220 of a manufacturing or processing production line, or otherwise being passed along a path past the apparatus. FIG. 12 shows how apparatus 20 for measuring pH in a sub-surface volume of a sample 10 may be provided to determine sub-surface pH in a sample object 10 which is rotating relative to the apparatus, whereby the apparatus 20 may determine pH of a sub-surface portion of the sample 10 which is located proximally to the apparatus at any particular time pH measurement also plays an important role in many industrial chemical processing facilities. Industries in which the present invention may conveniently be used include Oil & Gas, Chemicals, and Power & Energy, and indeed embodiments of the invention may also be used to determine pH in a variety of other, non-medical applications, for example in general manufacture and storage, in the control, monitoring and aging of food products, and in biopharmaceutical/pharmaceutical and other chemical product manufacture and subsequent testing and monitoring.

Although embodiments of the invention described above particularly focus on the detection of pH from the detected Raman spectral features, embodiments of the invention may additionally derive other parameters relating to the sub-surface volume from the Raman spectral features, such as temperature and chemical composition. The detection of sub-surface temperature in a diffusely scattering sample can be achieved as described in PCT/GB2016/051951, hereby incorporated by reference, for example by comparing intensities of corresponding Stokes and anti Stokes features in a Raman spectrum. Chemical composition data can be determined by identifying and measuring the intensities of particular spectral features or combinations of spectral features arising from particular chemical components.

Although particular embodiments and applications of the invention have been described, it will be apparent to the skilled person that various modifications and alterations can be made without departing from the scope of the invention.

What is claimed is:

1. A method of measuring pH in a subsurface volume of a diffusely scattering sample, comprising:
   directing probe light to an entry region on the sample surface;
   collecting said probe light from a collection region on the sample surface, following diffuse scattering within the sample, the collection region being spatially offset from the entry region;
   detecting one or more Raman spectral features in the collected probe light; and
   determining a pH of the subsurface volume from the one or more Raman spectral features;
   wherein the diffusely scattering sample or volume has a diffuse scattering transport length of less than 3 mm.

2. The method of claim 1 wherein determining a pH of the subsurface volume from the one or more Raman spectral features comprises determining the pH at least partly from intensities of one or more of the detected Raman spectral features.

3. The method of claim 1 wherein determining a pH of the subsurface volume from the one or more Raman spectral features comprises determining the pH at least partly from spectral position of one or more of the detected Raman spectral features.

4. The method of claim 1 comprising separately detecting said one or more Raman spectral features in the collected probe light for each of a plurality of different spatial offsets between said entry and collection regions.

5. The method of claim 4 wherein determining a pH of a subsurface volume from the one or more Raman spectral features comprises associating the Raman features from each of said plurality of different spatial offsets with a different depth or distribution of depth within the sample.

6. The method of claim 5 further comprising combining said Raman features from said different spatial offsets to determine a separate pH measurement for each of one or more depths or distributions of depth within the sample.

7. The method of claim 1 further comprising setting said entry and collection regions to be coincident or overlapping, and detecting one or more Raman spectral features in the collected probe light when said entry and collection regions are coincident or overlapping.

8. The method of claim 7 wherein determining a pH of a subsurface volume from the Raman spectral features comprises compensating said Raman spectral features detected when the entry and collection regions are spatially offset using the Raman spectral features detected when the entry and collection regions are coincident or overlapping.

9. The method of claim 7 further comprising determining a pH of the sample surface from the one or more Raman spectral features detected when the entry and collection regions are coincident or overlapping.

10. The method of claim 1 wherein the entry region comprises one or more segments which are located around a centrally disposed collection region.

11. The method of claim 10 wherein the entry regions comprises an annulus disposed around the collection region.

12. The method of claim 1 wherein the entry and collection regions are spatially offset by an offset in the range from 1 mm to 50 mm, and more preferably in the range from 3 mm to 20 mm.

13. The method of claim 1 wherein the subsurface volume is at least 2 mm beneath the sample surface.

14. The method of claim 1 wherein the subsurface volume comprises tissue of a human or animal subject, and the determined pH is a subsurface pH of the tissue.

15. The method of claim 14 wherein the sample surface is a surface of skin of the human or animal subject.

16. The method of claim 14 comprising determining an indication of cancerous tissue within the subsurface volume from the determined pH.

17. Apparatus for measuring pH within a volume of a diffusely scattering sample having a surface, comprising:
   a light source for generating probe light;
   delivery optics arranged to direct the probe light to an entry region on the surface;
   collection optics arranged to collect said probe light from a collection region on the surface, following scattering within the volume of the sample, the collection region being spatially offset from the entry region;
   a spectral analyser arranged to detect Raman spectral features in the collected probe light;
   a processor arranged to determine a pH of the volume from the Raman spectral features; and
   an offset driver arranged to provide a plurality of different spatial offsets between said entry and collection regions, the apparatus being arranged to separately detect said Raman spectral features for each different spatial offset, and to associate the Raman features from each of said plurality of different spatial offsets with a different depth or distribution of depths within the sample.

18. The apparatus of claim 17 wherein the processor is arranged to determine a pH of the volume from the Raman spectral features at least partly from one or more of intensities, spectral positions, and shapes of detected Raman spectral features.

19. The apparatus of claim 17 wherein the processor is arranged to combine said Raman features from said different spatial offsets to determine a separate pH for each of one or more depths or distributions of depth within the sample.

20. The apparatus of claim 17 arranged such that the entry and collection regions are spatially offset by an offset by a distance in the range from 1 mm to 50 mm, and more preferably in the range from 3 mm to 20 mm.

21. A method of measuring pH in a subsurface volume of a diffusely scattering sample, comprising:
   directing probe light to an entry region on the sample surface;
   collecting said probe light from a collection region on the sample surface, following diffuse scattering within the sample, the collection region being spatially offset from the entry region;

detecting one or more Raman spectral features in the collected probe light; and determining a pH of the subsurface volume from the one or more Raman spectral features, wherein the subsurface volume is beneath the sample surface by least twice the diffuse scattering transport length of probe light in the sample.

22. The method of claim 21 comprising separately detecting said one or more Raman spectral features in the collected probe light for each of a plurality of different spatial offsets between said entry and collection regions.

23. The method of claim 22 wherein determining a pH of a subsurface volume from the one or more Raman spectral features comprises associating the Raman features from each of said plurality of different spatial offsets with a different depth or distribution of depth within the sample.

24. The method of claim 23 further comprising combining said Raman features from said different spatial offsets to determine a separate pH measurement for each of one or more depths or distributions of depth within the sample.

25. The method of claim 21 wherein the entry region comprises one or more segments which are located around a centrally disposed collection region.

26. The method of claim 21 wherein the entry and collection regions are spatially offset by an offset in the range from 1 mm to 50 mm, and more preferably in the range from 3 mm to 20 mm.

27. The method of claim 21 wherein the subsurface volume is at least 2 mm beneath the sample surface.

28. A method of measuring pH in a subsurface volume of a diffusely scattering sample, comprising:

directing probe light to an entry region on the sample surface;

collecting said probe light from a collection region on the sample surface, following diffuse scattering within the sample, the collection region being spatially offset from the entry region;

detecting one or more Raman spectral features in the collected probe light; and determining a pH of the subsurface volume from the one or more Raman spectral features, wherein determining a pH of the subsurface volume comprises introducing reporter molecules into the subsurface volume, detecting one or more Raman spectral features of the reporter molecules, and determining a pH of the subsurface volume from the detected Raman features of the reporter molecules.

29. The method of claim 28 wherein the subsurface volume comprises tissue of a human or animal subject, and the reporter molecules are introduced into the subsurface volume by being administered to the subject.

30. The method of claim 28 wherein the reporter molecules are bound to nanoparticles to provide a surface enhanced Raman spectroscopy (SERS) effect for the detection of said one or more Raman spectral features.

31. The method of claim 30 wherein the nanoparticles are functionalised to bind to specific molecules of interest in the sample.

32. The method of claim 28 wherein the subsurface volume comprises tissue of a human or animal subject, and the determined pH is a subsurface pH of the tissue.

33. The method of claim 32 comprising determining an indication of cancerous tissue within the subsurface volume from the determined pH.

34. Apparatus for measuring pH within a volume of a diffusely scattering sample having a surface, comprising:

a light source for generating probe light;

delivery optics arranged to direct the probe light to an entry region on the surface;

collection optics arranged to collect said probe light from a collection region on the surface, following scattering within the volume of the sample, the collection region being spatially offset from the entry region;

a spectral analyser arranged to detect Raman spectral features in the collected probe light;

a processor arranged to determine a pH of the volume from the Raman spectral features, wherein the volume comprises reporter molecules, and the processor is arranged to determine pH from one or more Raman spectral features arising from the reporter molecules.

35. The apparatus of claim 34 wherein the reporter molecules are bound to nanoparticles to provide a surface enhanced Raman spectroscopy (SERS) effect for the detection of said one or more Raman spectral features arising from the reporter molecules.

* * * * *